United States Patent [19]

Abou-Gharbia

[11] Patent Number: 4,837,325
[45] Date of Patent: Jun. 6, 1989

[54] BETA-CARBOLINE H₁-RECEPTOR ANTAGONISTS

[75] Inventor: Magid A. Abou-Gharbia, Wilmington, Del.

[73] Assignee: American Home Products Corporation, New York, N.Y.

[21] Appl. No.: 179,105

[22] Filed: Apr. 8, 1988

Related U.S. Application Data

[63] Continuation-in-part of Ser. No. 19,089, Feb. 26, 1987, Pat. No. 4,766,124.

[51] Int. Cl.$^4$ ............................................ C07D 401/14
[52] U.S. Cl. .................................................. 544/372
[58] Field of Search ........................................... 544/372

[56] References Cited

U.S. PATENT DOCUMENTS 4,575,508  3/1986  Steiner et al. ........................ 514/292
4,663,456  5/1987  Abou-Gharbia ...................... 544/295

FOREIGN PATENT DOCUMENTS 22853  10/1964  Japan .

OTHER PUBLICATIONS

Derwent Abstract 20,387 (Jap. 2713/66; 2/21/66).

Primary Examiner—Anton H. Sutto
Assistant Examiner—Cecilia Shen
Attorney, Agent, or Firm—Richard K. Jackson

[57] ABSTRACT

The compounds

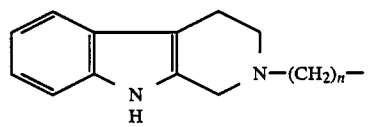

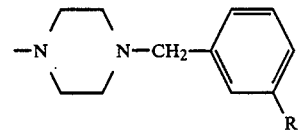

in which
R is halo or trifluoromethyl;
n is one of the integers 2, 3 or 4;
or a pharmaceutically acceptable salt thereof are useful as histamine H₁-receptor antagonists.

3 Claims, No Drawings

BETA-CARBOLINE H₁-RECEPTOR ANTAGONISTS

RELATED APPLICATION

This application is a continuation in-part of U.S. patent application Ser. No. 19,089, filed Feb. 26, 1987, by Magid A. Abou-Gharbia, entitled "Beta-Carboline H₁ Receptor Antagonists", now U.S. Pat. No. 4,766,124.

BACKGROUND OF THE INVENTION

Beta-carbolines possessing central nervous system activity are known. Japanese Pat. No. 22,853 discloses such compounds as sedatives and as possessing antihypertensive activity. Derwent 20,387 abstracts Japanese Pat. No. 2,713 which indicates that beta-carbolin-1-one derivatives act as central nervous system depressants as well as possessing antihistaminic activity. U.S. Pat. No. 4,575,508 to Steiner et al. discloses 1-aminoalkyl-beta-carboline derivatives useful as anti-arrhythmic agents. U.S. Pat. No. 4,663,456 discloses and claims the compound 2-[3-[4-[bis(4-fluorophenyl)methyl]]piperazinyl]-propyl]2,3,4,9-tetrahydro-1H-pyrido[3,4-b]indole and pharmaceutically acceptable salts thereof, which compound possesses antipsychotic and anxiolytic activity.

DESCRIPTION OF THE INVENTION

In accordance with this invention, there is provided a group of histamine H₁-receptor antagonists of the formula:

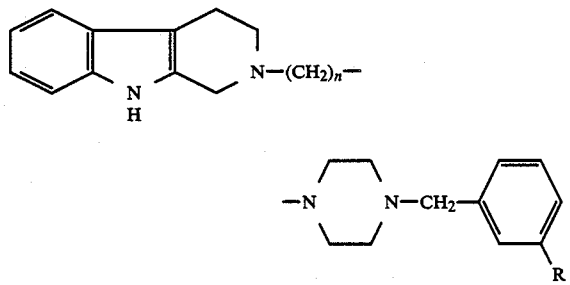

in which
R is halo or trifluoromethyl;
n is one of the integers 2, 3 or 4;
or a pharmaceutically acceptable salt thereof. These compounds exhibit excellent histamine H₁ receptor antagonist properties when administered orally or parenterally to a mammal in need of antihistaminic treatment.

In the compounds involved in this invention, the halogen substituent is chlorine, bromine or fluorine, preferably fluorine. The pharmaceutically acceptable salts are derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds are prepared by conventional methods whereby an appropriately substituted beta-carboline is alkylated with a dihaloalkane and the resulting N-(haloalkyl)-beta-carboline is coupled to an appropriately substituted piperazine reactant. The reactants employed are either commercially available or prepared by methods well within the skill of the medicinal chemist.

The histamine H₁-receptor antagonist activity of the compounds involved in this invention was established by subjecting them to the following standard test procedure for H₁-blocking activity.

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-6}$M. The contraction response after it equilibrated was noted as grams tension. Test drug was added, in the presence of histamine, to each bath to a final concentration of $1 \times 10^{-7}$M. The change in grams tension was noted and the percent reduction in grams tension calculated.

Following this procedure, which quadruplicate sets of tissues, the compound of Example 1 demonstrated 42 percent reduction in tissue contraction.

The pharmacological results obtained characterize the compounds of this invention as H₁-receptor antagonists useful in the treatment of mammals experiencing conditions such as asthma, hay fever, allergic rhinitis, atopic dermatitis, conjunctivitis, pruritis, and eczema, or other responses where histamine is released and acts on H₁ receptors. As such, they may be administered topically or systemically. Topical administration is advantageously achieved to the skin via creams, ointments or lotions, or via aerosol introduction into the respiratory tract. Systemic administration may be orally or parenterally, including the nasal, intrabronchial and rectal routes. In each instance, conventional formulations amenable to use in the desired administration route is appropriate. Hence, tablets and capsules may be prepared for oral administration, suppositories for rectal administration, isotonic aqueous solutions for intravenous, subcutaneous or intramuscular injection and in aerosol suspensions for inhalation.

A pharmaceutical carrier for the antihistaminic agents may be provided as a solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be a halogenated hydrocarbon or other pharmaceutically acceptable propellant.

Liquid pharmaceutical compositions which are sterile solutions or suspensions can be utilized by injection. Sterile solutions can also be administered intravenously.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

As is conventional in the use of antihistaminic agents, the appropriate dosage is determined on a subjective basis by initial administration of small amounts, ca 0.5–15 mg., followed by increasing quantities up to about 400 mg., depending upon the desired route of administration, until the desired symptomatic relief is obtained. The dosage is personalized in this manner for each patient based upon size, age, type of discomfort, degree of disability, etc., by the physician.

The compounds involved in this invention are prepared by the following illustrative procedure:

EXAMPLE 1

2,3,4,9-Tetrahydro-2-[3-[4-[3-(trifluoromethyl)benzyl]-1-piperazinyl]propyl]-1H-pyrido[3,4-b]indole To a stirred suspension of 2,3,4,9-tetrahydro-1H-pyrido[3,4-b]indole (1.3 g., 0.008 mol), freshly baked anhydrous potassium carbonate 3.3 g., 0.024 mol) in 70 ml. of dimethyl formamide, was added 4 g. (0.02 mol) of 1,3-dibromopropane. The reaction mixture was stirred for 1 hour and to this mixture was added 0.39 g. (0.0024 mol) of potassium iodide. The reaction mixture was stirred at room temperature overnight, the solvent was removed under vacuum and the solid cake was suspended in 100 ml. of water.

The aqueous suspension was extracted with chloroform (3×100 ml.), the chloroform layer was dried over anhydrous sodium sulfate and was evaporated under reduced pressure to afford a thick brown oil of the corresponding intermediate 2,3,4,9-tetrahydro-2-(3-bromopropyl)-1H-pyrido[3,4-b]indole. To 2.8 g. (0.01 mol) of this bromopropyl intermediate dissolved in 50 ml. of dimethylformamide, 5 ml. of triethylamine and 2.44 g. (0.01 mol) of 1-[3-(trifluoromethyl)-benzyl]piperazine were added. Stirring was continued at room temperature overnight. The solvent was removed under vacuum and the solid extracted with methylene chloride, evaporated to an oil, dissolved in ethanol and converted to trihydrochloride salt, monohydrate; m.p. 243°–245° C.

Analysis for: $C_{26}H_{31}F_3N_4.3HCl.H_2$. Calculated: C, 53.48; H, 6.21; N, 9.59. Found: C, 53.79; H, 6.05; N, 9.63.

EXAMPLE 2

2-[3-[4-[3-Fluorobenzyl]-1-piperazinyl]propyl]-2,3,4,9-tetrahydro-1H-pyrido[3,4-b]indole Following the procedure of Example 1, 2,3,4,9-tetrahydro-1H-pyrido[3,4-b]indole is alkylated with 1,3-dibromopropane. The intermediate 2,3,4,9-tetrahydro-2-(3-bromopropyl)-1H-pyrido[3,4-b]indole is then reacted with 1-[3-(trifluoromethyl)benzyl]piperazine to obtain the title compound.

What is claimed is:

1. A compound of the formula:

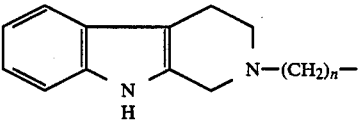

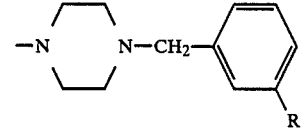

in which

R is halo or trifluoromethyl;

n is one of the integers 2, 3 or 4;

or a pharmaceutically acceptable salt thereof.

2. The compound which is 2,3,4,9-tetrahydro-2-[3-[4-[3-(trifluoromethyl)benzyl-1-piperazinyl]propyl]-1H-pyrido[3,4-b]indole, or a pharmaceutically acceptable salt thereof.

3. The compound which is 2-[3-[4-[3-fluorobenzyl]-1-piperazinyl]propyl]-2,3,4,9-tetrahydro-1H-pyrido[3,4-b]indole, or a pharmaceutically acceptable salt thereof.

* * * * *